United States Patent
Sekine et al.

(10) Patent No.: US 11,112,323 B2
(45) Date of Patent: Sep. 7, 2021

(54) BRAKE TESTING SYSTEM, BRAKE TESTING METHOD, AND PROGRAM FOR BRAKE TESTING SYSTEM

(71) Applicant: HORIBA, LTD., Kyoto (JP)

(72) Inventors: Daisuke Sekine, Kyoto (JP); Erika Matsumoto, Kyoto (JP); Takashi Matsuyama, Kyoto (JP)

(73) Assignee: HORIBA, LTD., Kyoto (JP)

( * ) Notice: Subject to any disclaimer, the term of this patent is extended or adjusted under 35 U.S.C. 154(b) by 162 days.

(21) Appl. No.: 16/568,328

(22) Filed: Sep. 12, 2019

(65) Prior Publication Data

US 2020/0096403 A1  Mar. 26, 2020

(30) Foreign Application Priority Data

Sep. 21, 2018  (JP) .............................. JP2018-177275

(51) Int. Cl.
*G01L 5/28* (2006.01)
*G01N 33/00* (2006.01)

(52) U.S. Cl.
CPC .............. *G01L 5/282* (2013.01); *G01L 5/288* (2013.01); *G01N 33/0027* (2013.01)

(58) Field of Classification Search
CPC . G01L 5/28; G01L 5/282; G01L 5/284; G01L 5/288; B60T 17/18; B60T 17/22; B60T 17/221; G01N 33/0027
See application file for complete search history.

(56) References Cited

U.S. PATENT DOCUMENTS

| | | | |
|---|---|---|---|
| 3,965,732 A * | 6/1976 | Cline | G01L 5/282 73/126 |
| 4,577,497 A | 3/1986 | Ray et al. | |
| 5,312,168 A * | 5/1994 | Breen | B60T 8/1708 188/106 P |
| 2009/0049901 A1* | 2/2009 | Fukamachi | G01L 5/286 73/121 |

FOREIGN PATENT DOCUMENTS

JP  2002-071527 A  3/2002

OTHER PUBLICATIONS

EESR dated Feb. 12, 2020 issued for European patent application No. 19 196 581.3, 9 pgs.
(Continued)

*Primary Examiner* — Benjamin R Schmitt
(74) *Attorney, Agent, or Firm* — Brooks Kushman P.C.

(57) ABSTRACT

A brake testing system of testing a brake of a vehicle driven on a bench having a rotating body, comprises a rotation control unit that controls to make the rotating body rotate at a predetermined rotational speed, a torque acquiring unit that acquires a torque value generated on the rotating body by the brake of the vehicle being operated, a time period acquiring unit that acquires a time period during which the brake of the vehicle is operated, and a braking work load calculating unit that calculates a work load of the brake based on the rotational speed of the rotating body controlled by the rotation control unit, the torque value acquired by the torque acquiring unit, and the time period acquired by the time period acquiring unit.

9 Claims, 6 Drawing Sheets

(56) References Cited

OTHER PUBLICATIONS

Akihiro Iijima et al., "Emission Factor for Antimony in Brake Abrasion Dusts as One of the Major Atmospheric Antimony Sources", Environmental Science & Technology, Apr. 1, 2008, vol. 42, No. 8, pp. 2937-2942.

Ahmed Fawwaz et al., "External Particle Shape Analysis and Its Effect on Tribological Performance of Disc Brake", XP055664961, DOI: 10.11113/jt.v78.5032, Aug. 31, 2016, Retrieved from the Internet on Feb. 4, 2020: URL:https//jurnalteknologi.utm.my/index.php/jurnalteknologl/article/download/5032/5708.

\* cited by examiner

BRAKE TESTING SYSTEM, BRAKE TESTING METHOD, AND PROGRAM FOR BRAKE TESTING SYSTEM

CROSS-REFERENCE TO RELATED APPLICATION

This application claims priority to Japanese Application No. 2018-177275, filed Sep. 21, 2018, the disclosure of which is incorporated in its entirety by reference herein.

TECHNICAL FIELD

The present invention relates to a brake testing system, a brake testing method, and a program for a brake testing system.

BACKGROUND ART

It is conventionally performed, for example, as disclosed in Patent Literature 1, that a test vehicle is driven with a predetermined driving mode on a chassis dynamometer and the exhaust gas emitted from the test vehicle is analyzed for the test of confirming whether or not the vehicle satisfies the standard of the exhaust gas regulation and the like.

CITATION LIST

Patent Literature

[Patent Literature 1] Japanese Unexamined Patent Application Publication No. 2002-071527

SUMMARY OF INVENTION

Technical Problem

By the way, as the awareness for environmental problems is recently increased, the request is also increased for performing not only the exhaust gas analysis described above, but also the brake test of quantitatively estimating the brake dust amount generated from the vehicle.

The present invention has been made to respond to such a request, and has an object to provide a brake testing system, a brake testing method, and a program for a brake testing system that can quantitatively estimate the brake dust amount generated from the vehicle.

Solution to Problem

While repeating earnest investigations in order to respond the above-described request, the present inventors got a viewpoint that there is a correlation between a brake dust amount generated due to the brake operation and a work load of the brake in the braking operation. Conventionally, no attempt has been performed for calculating a work load of the brake, and no one has grasped the correlation as described above. As the result of repeated earnest investigations, the present inventors have found that the work load of the brake can be calculated easily by performing bench tests with a chassis dynamometer, a brake dynamometer, and the like, and thus the correlation between the generation amount of brake dusts and the work load of the brake can be grasped so as to implement quantitative estimation of the brake dust amount, and then have reached the present invention.

In short, the brake testing system according to the present invention is a brake testing system of testing a brake of a vehicle driven on a bench having a rotating body, comprising a rotation control unit that controls to make the rotating body rotate at a predetermined rotational speed, a torque acquiring unit that acquires a torque generated on the rotating body by the brake of the vehicle being operated, a time period acquiring unit that acquires a time period during which the brake of the vehicle is operated, and a braking work load calculating unit that calculates a work load of the brake based on the rotational speed of the rotating body controlled by the rotation control unit, the torque acquired by the torque acquiring unit, and the time period acquired by the time period acquiring unit.

Such a configuration would easily calculate the work load of the brake in the braking operation, only by applying the brake to the test vehicle in a condition where the rotating body, on which the vehicle is mounted, is rotated at a predetermined rotational speed, and acquiring the torque generated on the rotating body at that time and the time period during which the brake is applied (in other words, the time period during which the torque is generated on the rotating body). Thus, it is possible to know the brake dust amount generated for the work load performed by the brake, for example, if the brake dust amount generated at the time of the braking operation is measured besides.

In order to grasp the correlation between the work load at the time in which the brake was operated and the brake dust amount generated by it, the above-described brake testing system may further comprise a brake dust amount calculating unit that calculates a brake dust amount generated by the brake being operated, and a storing unit that associates and stores the brake dust amount calculated by the brake dust amount calculating unit and the work load of the brake calculated by the braking work load calculating unit.

If such a configuration is implemented, for example, if an ECU mounted on a vehicle is configured to store or the like the speed at the time when the brake is stepped, the time period and the number of times with respect to the brake being stepped, and the like, so as to calculate the approximate integrated value of the work load performed by the brake, use of the above-described correlation would implement grasping the brake dust amount generated from the vehicle during driving.

As an aspect of the brake dust amount calculating unit, it is possible to mention a configuration that acquires the weight value of the brake pad of the brake before an brake operation and the weight value of the brake pad after the brake operation, and calculates the brake dust amount based on these acquired weight values.

Such a configuration would accurately calculate the amount of the brake dusts generated by the braking operation.

As an aspect of the above-described brake dust amount calculating unit, it is possible to mention a configuration that comprises a sampling unit that performs sampling of air containing the brake dusts generated by the brake being operated, an elemental analysis unit that performs elemental analysis on the sampled air subjected to the sampling by the sampling unit, and a brake dust amount calculating unit that calculates the brake dust amount contained in the sampled air based on an elemental analysis result of the elemental analysis unit.

Such a configuration could simultaneously calculate the work load of the brake at the time when the brake is applied to the vehicle and the brake dust amount by the use of a chassis dynamometer.

As a position where the sampling unit performs sampling of air, it is possible to mention the vicinity of the brake caliper unit of the brake, the vicinity of the wheel well unit of the wheel, around the vehicle, and the like. If the sampling omission of the generated brake dusts should be lesser, it is preferred to perform sampling of air from the wheel well unit of the wheel. This could implement accurately knowing the relationship between the work load at the time when the brake was operated and the brake dust amount generated by it.

In addition, the brake testing method according to the present invention is for testing a performance of a brake of a vehicle driven on a bench having a rotating body, and comprises a rotation control step for controlling to make the rotating body rotate at a predetermined rotational speed, a torque acquiring step for acquiring a torque generated on the rotating body by the brake of the vehicle being operated, a time period acquiring step for acquiring a time period during which the brake of the vehicle is operated, and a braking work load calculating step for calculating a work load of the brake based on the rotational speed of the rotating body controlled in the rotation control step, the torque acquired in the torque acquiring step, and the time period acquired in the time period acquiring step.

The above-described brake testing method is preferred to further comprise a brake dust amount calculating step for calculating a brake dust amount generated by the brake being operated, and a storing step for associating and storing the brake dust amount calculated in the brake dust amount calculating step and the work load of the brake calculated in the work load calculating step.

In addition, it is preferred to further comprise an unit brake dust amount calculating step for calculating an unit brake dust amount which is a brake dust amount per an unit work load of the brake.

In addition, the program for a brake testing system according to the present invention is to test a performance of a brake of a vehicle driven on a bench having a rotating body, and to make a computer implement a function as a rotation control unit that controls to make the rotating body rotate at a predetermined rotational speed, a function as a torque acquiring unit that acquires a torque generated on the rotating body by the brake of the vehicle being operated, a function as a time period acquiring unit that acquires a time period during which the brake of the vehicle is operated, and a function as a braking work load calculating unit that calculates a work load of the brake based on the rotational speed of the rotating body controlled by the rotation control unit, the torque acquired by the torque acquiring unit, and the time period acquired by the time period acquiring unit.

Such a brake testing method and a program for a brake testing system can obtain effects similar to the above-described brake testing system.

Advantageous Effects of Invention

In accordance with the present invention configured as described above, it is possible to provide a brake testing system, a brake testing method, and a program for the brake testing system that can use a chassis dynamometer so as to test the brake performance of the vehicle.

DESCRIPTION OF EMBODIMENTS

An embodiment of the brake testing system according to the present invention is explained below, referring to figures.

1. Brake Testing System

The brake testing system 100 of the present embodiment is to make a test vehicle V, which is a completed vehicle having a brake B, be driven on a chassis dynamometer 2 so as to test a performance of the brake B of this test vehicle V. Specifically, while calculating the work load performed by the brake B at the time when the brake B is operated in a condition where the test vehicle V is driven on the chassis dynamometer 2, it calculates the amount of brake dusts generated from the brake B.

Figure 1:
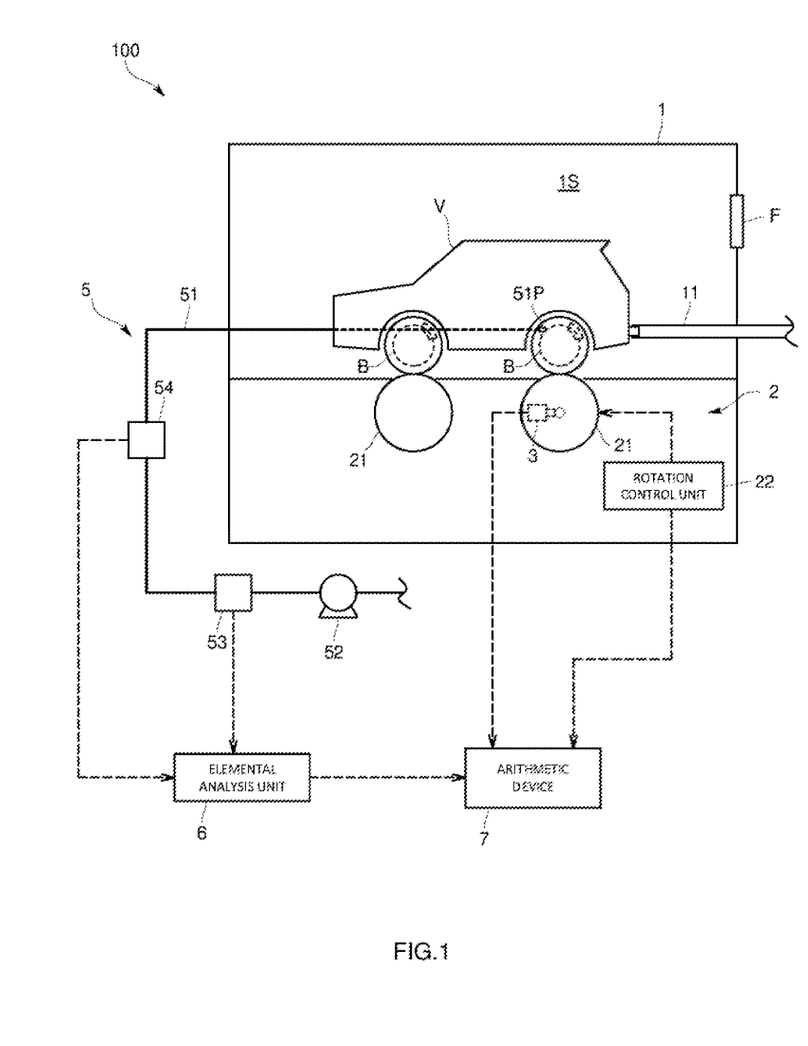
FIG. 1 is a whole schematic view of a brake testing system of the present embodiment.

In particular, as shown in FIG. 1, this brake testing system 100 includes a chamber 1 in which the test vehicle V is arranged, a chassis dynamometer 2 that includes a chassis roller 21 (corresponding to the "rotating body" according to the present invention, and hereinafter being simply referred to as roller, too) configured to rotate on which the wheel of the test vehicle V is mounted, a torque acquiring unit 3 that acquires a torque applied on the rotation axis of a roller 21, a sampling unit 5 that samples air in the chamber 1, an elemental analysis unit 6 that analyzes the sampled air sampled by the sampling unit 5, and an arithmetic device 7 that calculates the work load of the brake B and the amount of brake dusts.

The chamber 1 includes a sealed space IS being substantially sealed in which, for example, the test vehicle V is arranged, and includes an emission mechanism 11 emitting the exhaust gas emitted from the test vehicle V to the outside of the chamber 1. The emission mechanism 11 is a pipe arrangement that communicates the exhaust pipe of the test vehicle V and the outside of the chamber 1.

The chassis dynamometer 2 includes a roller 21 which is a rotating body, and a motor not shown in figures which is connected to the roller 21 and rotates this. Specifically, the roller 21 is a rotating drum, an endless belt (flat belt), or the like, for example. Here, a roller 21 is provided for a front wheel of the test vehicle V and another roller 21 is provided for a rear wheel of the test vehicle V. However, one roller 21 might be provided for the front wheel or the rear wheel.

The chassis dynamometer 2 of the present embodiment includes a rotation control unit 22 that controls to rotate the roller 21 at a predetermined rotational speed. The rotation control unit 22 includes a CPU, a memory, an A/D converter, a D/A converter, and the like. Then, the CPU and the peripheral equipments cooperate in accordance with the program stored in a predetermined area of the memory, to control the output of the motor so as to rotate the roller 21 at the predetermined rotational speed. The rotation control unit 22 of the present embodiment is configured to control the output of the motor so as to continuously rotate the roller 21 at the fixed rotational speed.

The torque acquiring unit 3 is specifically a torque sensor attached to the rotation axis of the roller 21. This torque sensor utilizes a strain gage. The torque acquiring unit 3 is configured to continuously acquire torque values applied on the rotation axis of the roller 21. Here, it is configured to continuously acquire torque values applied on the rotation axis of the roller 21 at least in the period during which the test vehicle V is driven on the roller 21.

The sampling unit 5 is to sample the air in the chamber 1. In particular, this sampling unit 5 is provided with a collection pipe 51 whose one end part (collection port 51P) is open in the chamber 1, and with a suction pump 52 installed on the collection pipe 51 for suctioning the air from the collection port 51P. Then, the collection pipe 51 is provided with a capturing filter 54 for capturing brake dusts contained in the air sampled by the collection port 51P, and a flow rate sensor 53 that measures the flow rate of the air flowing in the collection pipe 51.

The collection port 51P of the collection pipe 51 is configured to open in the vicinity of a wheel well unit of the rear wheel of the test vehicle V. It should be noted that the collection port 51P might be configured to open in the vicinity of a brake caliper unit or around the test vehicle V in the chamber 1. It should be noted that, in the case where a vehicular speed fan for simulating the vehicular speed wind is installed in the chamber 1, the collection port 51P is preferred to be configured so as to open forward at a position behind the brake B. Since brake dusts generated by the wind from the vehicular speed fan tend to be easily blown backward, such a configuration of the collection port 51P could reduce the sampling omission.

The capturing filter 54 is to capture particles in the air being sampled, and might be a separate type in which each piece is separated or a winding type in which a supplying roll and a winding roll are utilized. As for the material of the capturing filter 54, for example, PTFE-coated glass fiber, PTFE, or the like might be given.

The elemental analysis unit 6 is to perform elemental analysis on the air sampled by the sampling unit 5. In particular, the elemental analysis unit 6 is to perform the elemental analysis on particles captured by the capturing filter 54. This elemental analysis unit 6 is, specifically, a fluorescence X-ray analysis device that is a device to irradiate X-ray to the sample, and then to detect the generated fluorescence X-ray, so as to perform analysis on the metallic element. The above-described sample is the capturing filter 54 having captured particles. The elemental analysis unit 6 of the present embodiment is to perform quantitative analysis on the density (for example, mass concentration (%)) and the mass (g) of the elements contained in the particles captured by the capturing filter 54. It should be noted that, in the case where the capturing filter 54 is the separate type, the capturing filter 54 is removed from the sampling unit 5 and is set to the elemental analysis unit 6, and then the elemental analysis is performed. In addition, in the case where the capturing filter 54 is the winding type, the elemental analysis unit 6 is installed in the vicinity of the capturing filter 54 and then the elemental analysis is performed without removal of the capturing filter 54 from the sampling unit 5. In this case, the capturing filter 54 of the winding type and the elemental analysis unit 6 might be integrally configured so as to be one device (elemental analysis device with the filter 54).

Figure 2:
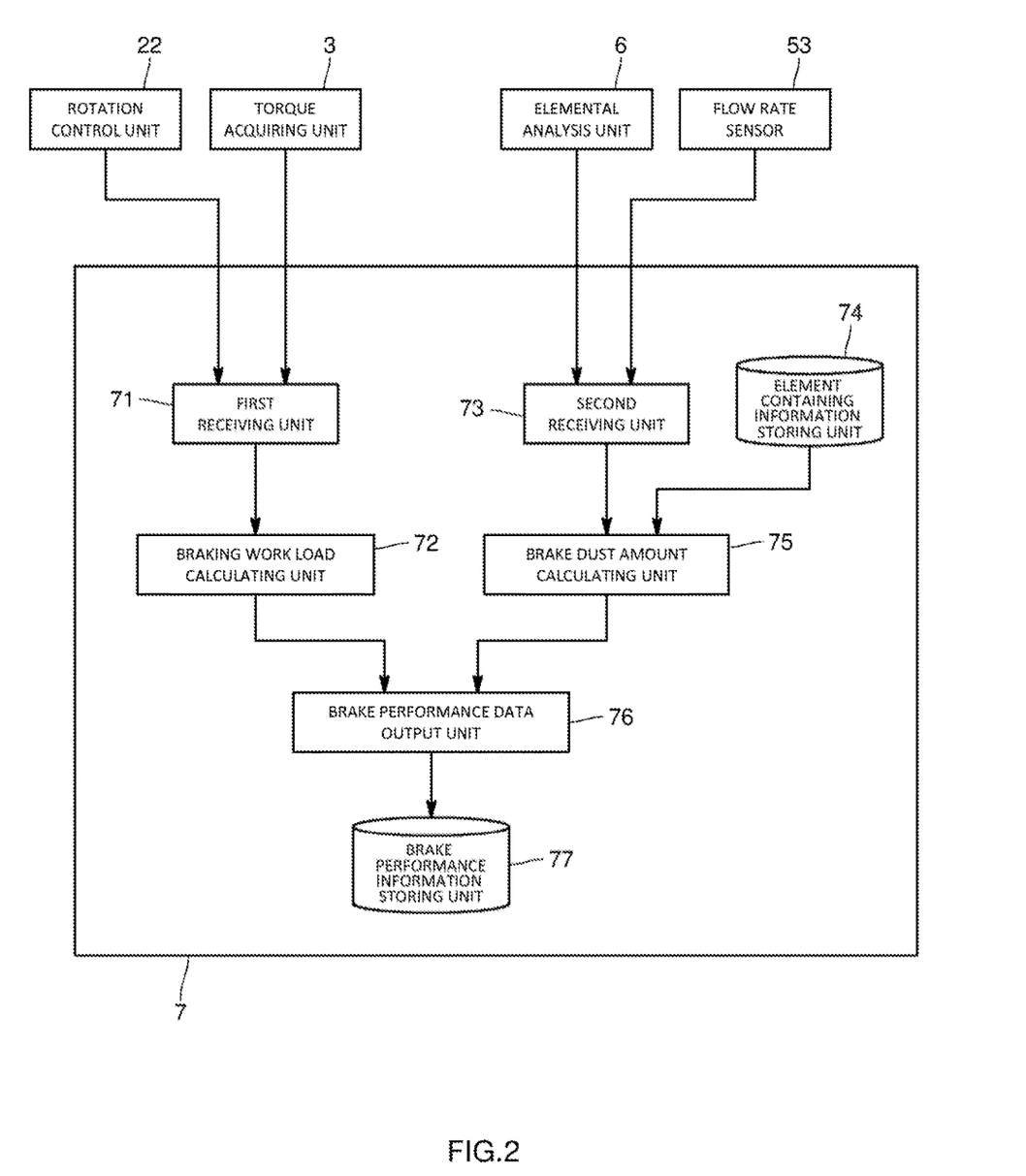
FIG. 2 is a functional block diagram showing a function of an arithmetic device according to the same embodiment.

The arithmetic device 7 is a dedicated or generic computer including a CPU, an internal memory, an input-output interface, an A/D converter, and the like. Then, since the CPU and the peripheral equipment cooperate based on the program for the brake testing system 100 stored in the internal memory, this arithmetic device 7 implements functions as the first receiving unit 71, the braking work load calculating unit 72, the second receiving unit 73, the element containing information storing unit 74, the brake dust amount calculating unit 75, the brake performance data generating unit 76, and the brake performance information storing unit 77 (corresponding to the storing unit according to the present invention), as shown in FIG. 2. Each unit is explained below.

The first receiving unit 71 receives the rotational speed data for the roller 21 controlled by the rotation control unit 22 and then sends it to the braking work load calculating unit 72.

In addition, the first receiving unit 71 receives torque data acquired by the torque acquiring unit 3 and, based on this, acquires the braking time being a time period during which the brake B of the test vehicle V is operated. In other words, the first receiving unit 71 in the present embodiment includes a function as the time period acquiring unit. The braking time means a time period during which a higher torque is applied on the rotation axis of the roller 21 than the case of normal driving (the case of no step on the brake B), for example, since a test driver stepped on the brake B of the test vehicle V. The first receiving unit 71 includes, specifically, a timer function incorporated into the arithmetic device 7, and is configured to acquire a time period, as the braking time, from a condition in which the torque value received from the torque acquiring unit 3 becomes above a predetermined value to a condition in which the torque value received from the torque acquiring unit 3 becomes below the predetermined value. Then, the first receiving unit 71 sends the braking time data representing the braking time and the braking time torque data representing the torque value at this braking time, to the braking work load calculating unit 72. It should be noted that, in the present embodiment, the torque value at the braking time is treated as an average value of torque values acquired in the braking time.

The braking work load calculating unit 72 is to calculate the work load of the brake B based on the rotational speed data, the braking time torque data, and the braking time data received from the first receiving unit 71. In particular, the braking work load calculating unit 72 utilizes R (rpm) as the rotational speed of the roller 21 represented by the rotational speed data, T (N*m) as the torque value applied to the rotation axis of the roller 21 represented by the braking time torque data, and tr (s) as the time represented by the braking time data, so as to calculate the power P (kW) and the work load W (kJ) of the brake B at the braking operation time with the following formula. Then, the braking work load calculating unit 72 sends the calculated work load W to the brake performance data generating unit 76.

<Power (P) of Brake>

$$P = 2\pi \times T \times R/(60 \times 1000)$$

<Work Load (W) of Brake>

$$W = P \times t_B = 2\pi \times T \times R \times t_B/(60 \times 1000)$$

The element containing information storing unit 74 stores containing information for one or a plurality of elements contained in the brake B. This containing information is digital data, and might include not only the already-known density (for example, mass concentration (%)) of one or a plurality of elements contained in the brake B, but also a composition ratio or a containing ratio for said one or said plurality of elements. In addition, the containing information might be input by a user in advance, or sent from a server or the like via Internet. The element containing information storing unit 74 of the present embodiment stores the containing information about one or a plurality of elements contained in the brake pad.

The second receiving unit 73 receives the elemental analysis information obtained by the elemental analysis unit 6. This elemental analysis information might include not only the measured density (for example, mass concentration (%)) of a plurality of elements contained in the particles captured by the capturing filter 54, but also the composition ratio, or the containing ratio of said plurality of elements, or the like. In addition, the second receiving unit 73 receives the flow rate data of air flowing in the collection pipe 51 obtained by the flow rate sensor 53. Then, the second receiving unit 73 sends the received elemental analysis information and flow rate data to the brake dust amount calculating unit 75.

The brake dust amount calculating unit 75 is to calculate the brake dust amount contained in the sampled air, based on the elemental analysis information and the flow rate data received by the second receiving unit 73 and the containing information stored in the element containing information storing unit 74.

In particular, the brake dust amount calculating unit 75 measures weight (g*m/s$^2$) of titanium (Ti) based on the elemental analysis information (titanium: $M_{Ti}$). It should be noted that, as for the measuring method of the weight of each component, weight difference between the capturing filter 54 before capturing and the capturing filter 54 after capturing might be calculated and then the weight difference might be multiplied with the containing ratio of each component obtained by the elemental analysis device, or the capture weight might be calculated based on the transmission intensity of β ray obtained by, for example, irradiating β ray to the capturing filter 54 after capturing and then the capture weight might be multiplied with the containing ratio of each component obtained with the elemental analysis device.

In advance, with respect to the containing ratio of titanium of the brake pad, the weight percentage (%) is measured with the elemental analysis device (titanium: $R_{Ti}$ %). It should be noted that this containing ratio of titanium is stored in the element containing information as the containing information.

In addition, the sampling flow rate of the sampling unit 5 (that is, flow rate data of the flow rate sensor 53) is expressed as X (m$^3$/min), and the sampling time of the sampling unit 5 is expressed as $t_s$ (min).

At that time, the brake dust amount calculating unit 75 utilizes the following formula so as to calculate the brake dust amount (g*m/s$^2$) contained in the air being sampled. It should be noted that the abrasion amount of the brake pad due to operation of the brake B is much larger than the abrasion amount of the brake rotor. Thus, in the present embodiment, the dust generation amount from the brake pad is regarded as the brake dust amount generated from the entire brake.

<Brake Dust Amount ($m_B$)>

$$m_B = (M_{Ti}/R_{Ti}) \times t_s$$

The above-described brake dust amount is an amount contained in the air being sampled, and a brake dust amount contained in air being not-sampled is not included. Thus, the brake dust amount calculating unit 75 also could utilize the following method so as to calculate the whole amount ($m_{TOTAL}$) of the brake dusts, generated from the brake B, from the brake dust amount ($m_B$) contained in the sampled air, based on the volumetric capacity ($V_C$) of the chamber 1 and the integration flow rate ($Q_S$) of the sampled air. Then, the brake dust amount calculating unit 75 sends the calculated whole amount $m_{TOTAL}$ of the brake dusts to the brake performance data generating unit 76.

<Whole Amount ($m_{TOTAL}$) of Brake Dusts Generated from Brake>

$$m_{TOTAL} = m_B \times V_C/Q_S$$

The brake performance data generating unit 76 receives the work load of the brake B calculated by the braking work load calculating unit 72 and the whole amount of the brake dusts calculated by the brake dust amount calculating unit 75, and associate them so as to generate a set of brake performance data. Here, the brake performance data generating unit 76 associates the work load of the brake B working during a predetermined time period and the whole amount of brake dust generated during the same predetermined time period, and generates this as a set of brake performance data. The brake performance data generating unit 76 is configured to generate a new pair of brake performance data every time the test vehicle V is subjected to the test drive. Then, every time a set of brake performance data is generated, the brake performance data generating unit 76 sends this to the brake performance information storing unit 77.

The brake performance information storing unit 77 stores the brake performance data received from the brake performance data generating unit 76. The brake performance information storing unit 77 is configured to accumulate and store the brake performance data received from the brake performance data generating unit 76. In other words, when the brake performance information storing unit 77 receives a new pair of brake performance data, the brake performance information storing unit 77 stores this as different data from the previously-received brake performance data.

2. Brake Testing Method

Figure 3:
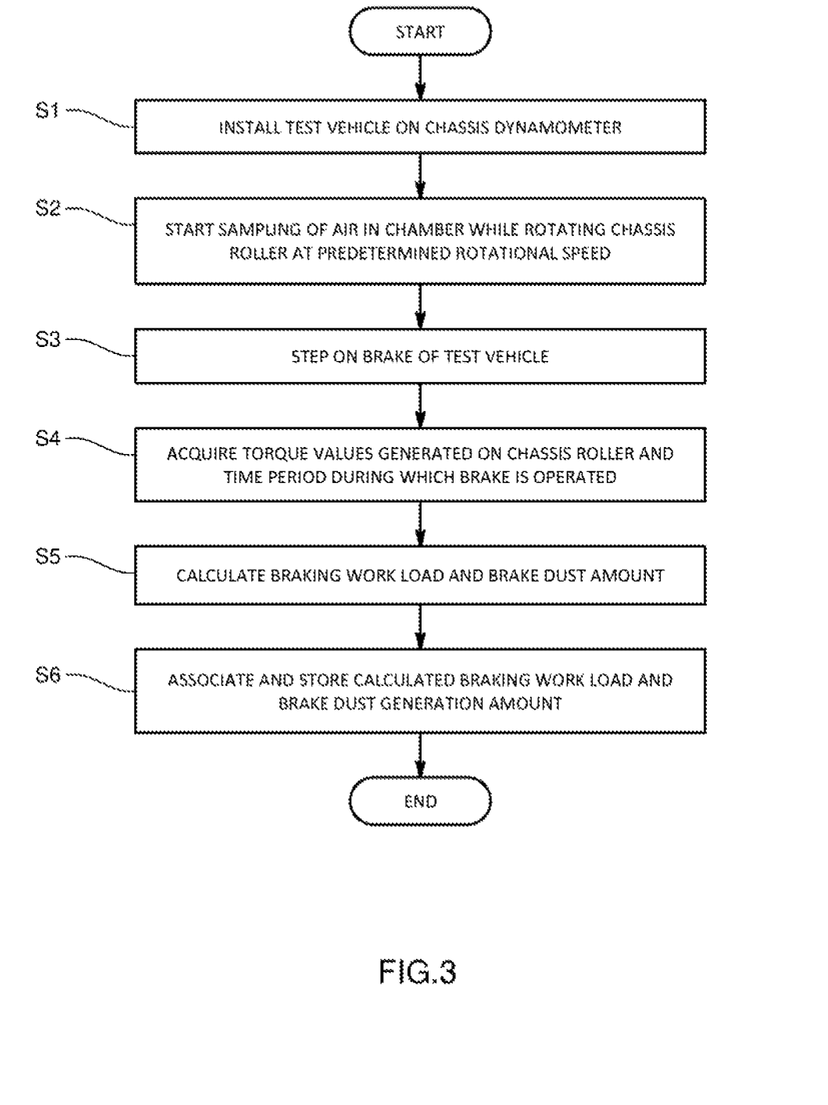
FIG. 3 is a flowchart showing a procedure of a brake testing method of the same embodiment.

The brake testing method utilizing the above-described brake testing system 100 is explained below, referring to FIG. 3.

Firstly, the test vehicle V including the brake B is installed on the chassis dynamometer 2 (Step S1).

Next, in a condition where a gear of the test vehicle V is neutral, the motor is controlled to output so as to make the chassis roller 21 rotate at a fixed rotational speed (Step S2). Here, the rotational speed of the chassis roller 21 is controlled to make the vehicle speed of the test vehicle V become 20 km/h. The wheel of the test vehicle V kept on the chassis roller 21 would rotate at a rotational speed corresponding to the rotation of the chassis roller 21. It should be noted here that the sampling of air in the chamber 1 is started by the sampling unit 5 at the same time as rotation start of the chassis roller 21.

Figure 4:
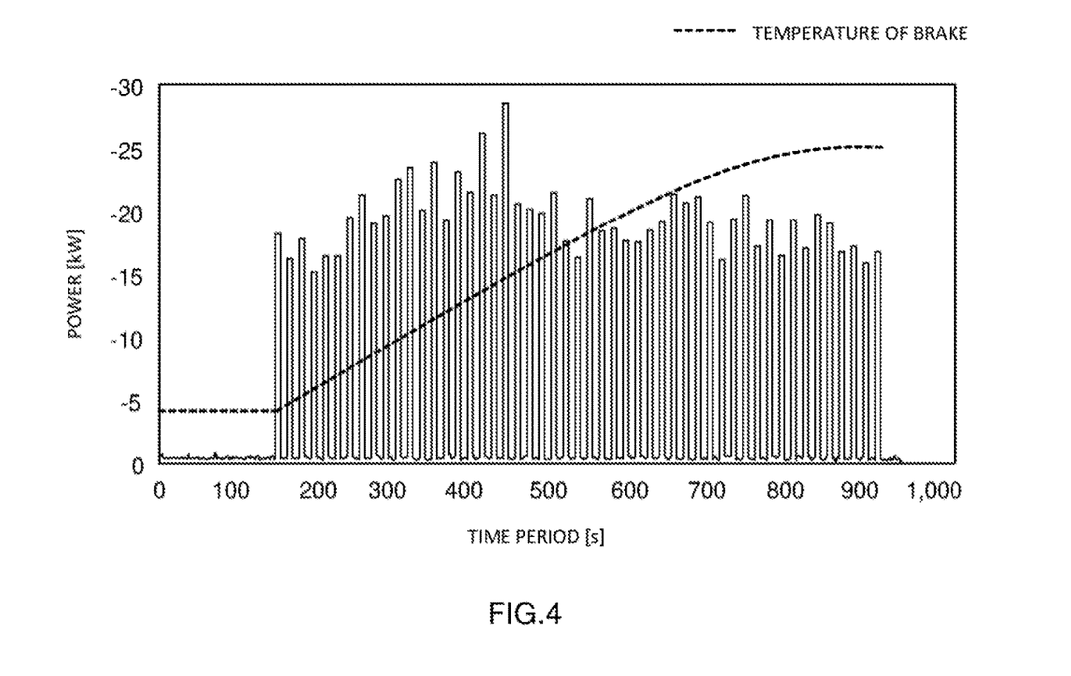
FIG. 4 is a graph showing one example way of applying brakes in the brake testing method of the same embodiment.

A test driver steps on the brake B of the test vehicle V in a condition where the chassis roller 21 rotates at the predetermined rotational speed (Step S3). Then, since braking force works between the tire and the chassis roller 21 but the chassis roller 21 continues rotating at a fixed rotational speed R, the torque applied on the rotation axis of the chassis roller 21 increases. Here, the test driver keeps stepping on the test brake B continuously during a predetermined time period as shown in FIG. 4. It should be noted that the brake B of the test vehicle V might be stepped on intermittently like pumping.

While the brake B is stepped on by the test driver, the torque values applied on the rotation axis of the chassis roller 21 are acquired by the torque sensor and the braking time period is acquired by the arithmetic device 7 based on the torque values (Step S4).

After the above-described Step S3 and Step S4 are repeated by a predetermined number of times, the braking work load calculating unit 72 multiplies the rotational speed of the roller 21, the torque value applied on the rotation axis of the roller 21 at the operation time of the brake B, and the time period during which the brake B is operated, so as to calculate the total work load of the brake B for the above-described test drive. In addition, the total brake dust amount generated in the above-described test drive is calculated by the brake dust amount calculating unit 75 (Step S5).

Finally, the brake performance data generating unit 76 generates the brake performance data in which the work load of the brake B and the brake dust amount generated in the test drive are associated, and stores this in the brake performance information storing unit 77 (Step S6).

Then, the rotational speed of the chassis roller 21 and the time period during which the brake B is operated are changed to differentiate the calculated braking work load W. and the above-described Steps S2 to S6 are repeated by a plurality of times. Specifically, for example, the vehicle speed of the test vehicle V is changed from 10 km/h to 100 km/h by 10 km/h, the brake B is operated at each vehicle speed during a predetermined time period, the braking work load and the brake dust amount for this braking operation are calculated, and the brake performance data, in which these are associated, is generated and stored in the brake performance information storing unit 77. Alternatively, for example, the vehicle speed of the test vehicle V might be kept to be 20 km/h and the time period during which the brake B is operated might be changed.

Figure 6:
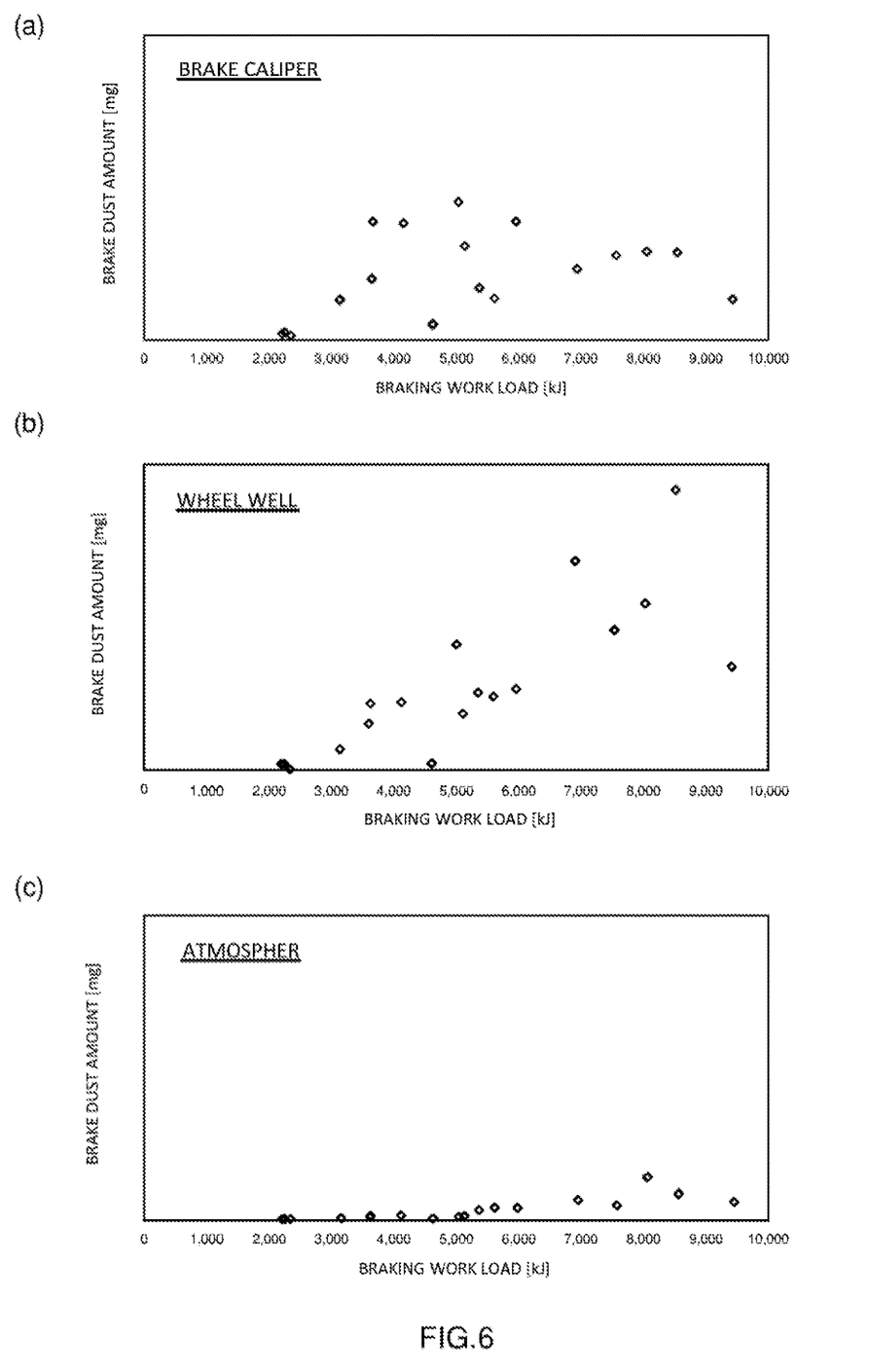
FIG. 6 is a graph showing a relationship between the braking work load and the brake dust amount obtained by the brake testing system of the present embodiment.

Relationships between the work load of the brake B and the brake dust amount, which are obtained by the above-described brake testing system 100 and the brake testing method, are shown in FIGS. 6 (a) to (c). FIG. 6 (a) is a graph showing a result of sampling from the vicinity of the brake caliper unit, (b) is a graph showing a result of sampling from the vicinity of the wheel well unit, and (c) is a graph showing a result of sampling from atmosphere in front of the vehicular speed fan. From these figures, it is understood that the amount of the generated brake dusts becomes larger in proportion to the work load of the brake B. It is understood that, when the sampling from the vicinity of the wheel well unit of the wheel is performed, this tendency becomes the most remarkable (FIG. 6 (b)). Thus, it is understood that the sampling from the vicinity of the wheel well unit can implement less sampling omission of the generated brake dusts and more accurate knowledge of the correlation between the work load of the brake B and the generated brake dust amount, than the sampling from the vicinity of the brake caliper unit and from the scaled space IS around the test vehicle V.

According to the brake testing system 100 of the present embodiment configured as described above, it is possible to easily calculate the work load of the brake B for the braking operation, only by applying the brake B on the test vehicle V in the condition where the chassis roller 21, on which the test vehicle V being a completed vehicle is mounted, is rotated at a predetermined rotational speed, and by acquiring the torque generated on the chassis roller 21 at this time and the time period during which the brake B is applied.

In addition, since the elemental analysis unit 6 is provided to calculate the brake dust amount together with calculation of the work load of the brake B so that the brake dust amount and the work load of the brake B are associated and stored, it is possible to know the correlation between the work load at the time when the brake B is operated and the brake dust amount generated by it. Thus, if an ECU mounted on a vehicle is, for example, configured to perform storing or the like of the speed at the time when the brake B is stepped on, the time period during which the brake B is stepped on, the number of times at which the brake B is stepped on, and the like, so as to grasp an approximate integrated value of the work load performed by the brake B, it is possible to grasp the brake dust amount generated from the vehicle during driving by utilizing the correlation between the above-described work load of the brake B and the generated brake dust amount.

In addition, since the sampled air introduced into the elemental analysis unit 6 is sampled from the vicinity of the wheel well unit of the wheel, it is possible to reduce the sampling omission of the brake dust and to accurately know the relationship between the work load at the time when the brake B is operated and the brake dust amount generated by it.

It should be noted that the present invention is not limited to the above-described embodiment.

Figure 5:
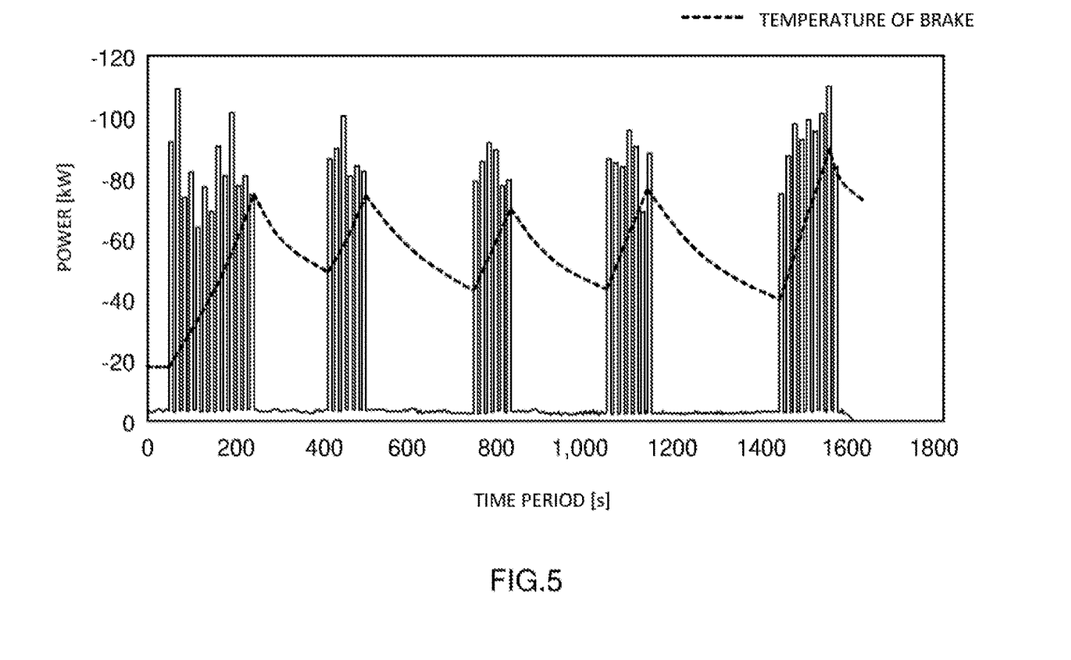
FIG. 5 is a graph showing another example way of applying brakes in the brake testing method of the same embodiment.

According to a brake testing method of another embodiment, in Step S3, as shown in FIG. 5, it might be configured that the brake B is released after the brake B is operated, and the brake B is operated again after the temperature of the brake B becomes below a predetermined value. Such a configuration could prevent the temperature of the brake B from being increased excessively.

Although the rotation control unit 22 controls the output of the motor to continue the roller 21 rotating at a fixed rotational speed in the above-described embodiment, the present invention is not limited to this. In another embodiment, it might be configured to control the output of the motor so as to change the rotational speed of the roller 21 during the driving test.

Although the braking work load calculating unit 72 of the above-described embodiment calculates the work load of the brake B with the braking time during which the brake B is operated and the average value of the torque values acquired during this braking time, this invention is not limited to this. For example, as shown by the following formula, the work load W might be calculated by integrating the product of the torque value T applied on the rotation axis of the roller 21 and the rotational speed R of the roller 21 by the time of the braking time $t_B$.

$$W = \frac{2\pi}{60 \times 1000} \int_{t_0}^{t_0 + t_B} T(t) \cdot R(t) dt \qquad \text{[Formula 1]}$$

Here, T (t) is a torque value applied on the rotation axis of the roller 21 at the time t, R (t) is a rotational speed of the roller 21 at the time t, and to is a time at which the braking operation is started.

Although the time period during which the brake B is operated means the time period from a condition in which the torque value received by the torque acquiring unit 3 becomes above a predetermined value to a condition in which the torque value received by the torque acquiring unit 3 becomes below the predetermined value in the above-described embodiment, the present invention is not limited to this. In another embodiment, the driving of the test vehicle V might be performed by an automatically driving robot and then the time during which the brake B is operated might be determined on the basis of a program previously incorporated in this automatically driving robot for stepping on the brake B. In addition, a test driver might measure the total time during which the brake B is stepped on in the driving test with a stopwatch or the like, and the time period during which the brake B is operated might be acquired by inputting this measured time into the arithmetic device 7. In addition, the time period during which the brake B is operated might be determined in advance, and then this might be inputted into the arithmetic device 7 in advance. In this case, it is enough that the test driver in the driving test operates the brake B during the time period determined in advance.

In another embodiment, the brake performance data generating unit 76 might be configured to calculate the unit brake dust amount that is a brake dust amount by the unit work load of the brake B (in other words 1 kJ) based on the received braking work load and brake dust amount, and to store this as the brake performance data in the brake performance information storing unit 77.

Figure 7:
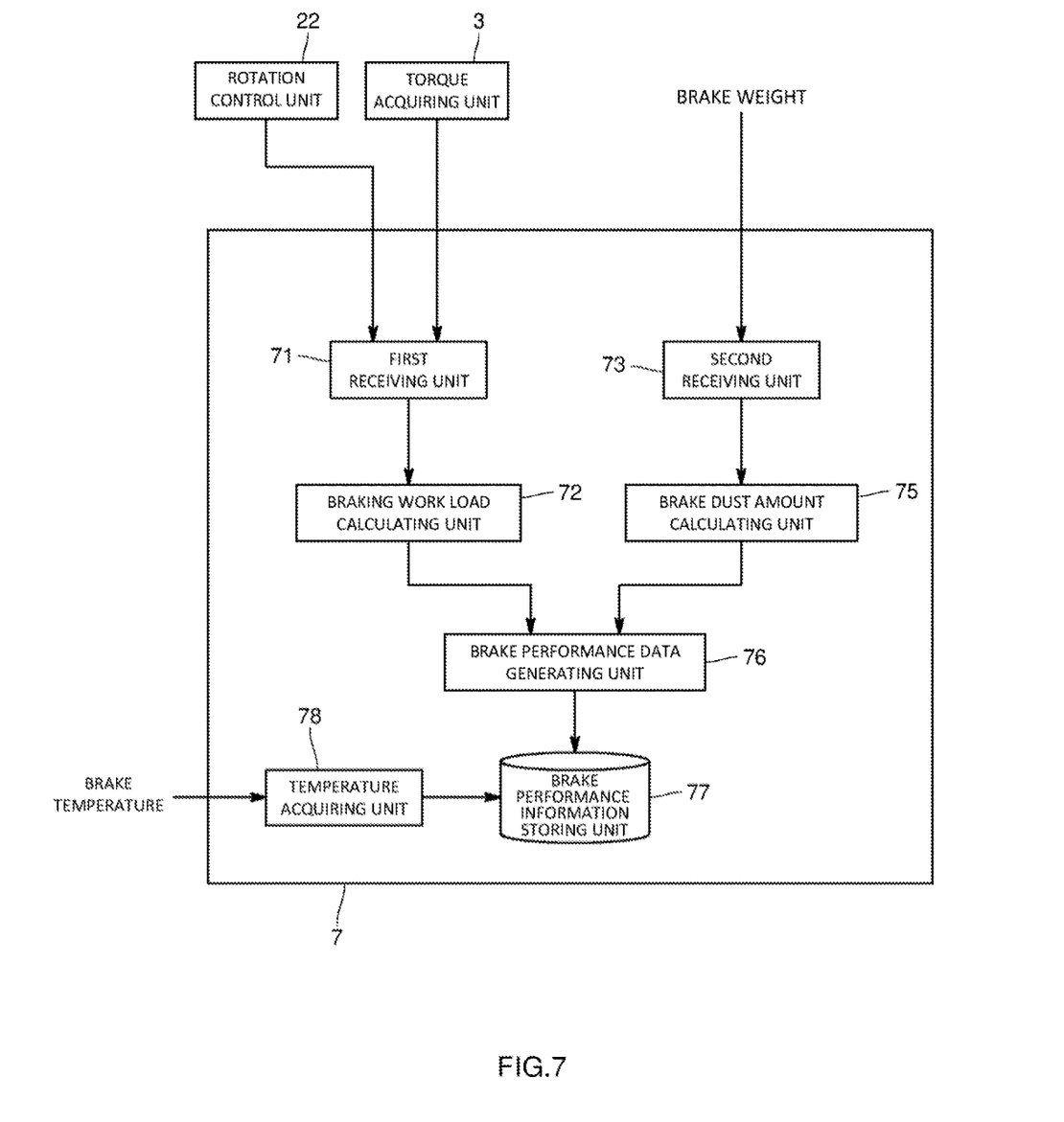
FIG. 7 is a functional block diagram showing a function of an arithmetic device according to another embodiment.

In another embodiment, as shown in FIG. 7, the arithmetic device 7 might further include a temperature acquiring unit 78 that acquires a temperature of the brake B in a period during which the brake B is operated. This temperature acquiring unit 78 acquires the temperature of the brake pad from a thermometer, such as a radiation thermometer not shown in figures, for example, and then associates this acquired temperature with the work load calculated by the braking work load calculating unit 72 and the brake dust amount calculated by the brake dust amount calculating unit 75 so as to store in the brake performance information storing unit 77. Thus, it is possible to know the relationship between the temperature of the brake (for example, brake pad) and the work load of the brake B, and between the temperature of the brake and brake dust amount.

Although the brake dust amount is calculated in the above-described embodiment by converting the measured weight of the titanium, the present invention is not limited to this. The brake dust amount might be calculated by converting the measured weight of other metallic element, such as copper (Cu). In addition, as shown in the following formula, the brake dust amount might be calculated by averaging dust amounts of the brake pad converted from measured weights of a plurality of metallic elements (for example, titanium and copper).

$$m_B = [\text{Average of } (M_{Ti}/R_{Ti}) \text{ and } (M_{Cu}/R_{Cu})] \times t_s$$

In addition, as shown in FIG. 7, the brake dust amount calculating unit 75 might acquire the weight value of the brake pad before the brake B is operated (in other words, before the driving test) and the weight value of the brake pad after the brake is operated (in other words, after the driving test), and calculate the brake dust amount with these values. Specifically, it is possible to treat the value, in which the weight value of the brake B after the driving test is subtracted from the weight value of the brake B before the driving test, as the brake dust amount. In this case, it might be configured that the weight values of the brake B before and after the driving tests are directly measured with a weigher by an operator and directly input into the second receiving unit 73. In addition to this, the brake dust amount might be calculated by sampling air in the chamber 1 and analyzing it as described above.

In another embodiment, the brake testing system 100 might be combined with a system in which the exhaust gas emitted from the test vehicle V driven on the chassis dynamometer 2 of the above-described embodiment is collected by an exhaust gas sampling device, and the predetermined component contained in the exhaust gas is analyzed by an exhaust gas analyzing device.

Although the brake dust amount in the above-described embodiment is with respect to the measurement for the brake dusts only of the brake pad, it might be with respect to the measurement for the brake dust of both of the brake pad and the brake rotor. In addition, it is possible as for the type of the brake B to utilize, for example, a disk brake or a drum brake. In this case, the storing unit stores containing information about elements of the brake shoe and/or containing information about elements of the brake drum.

Although the air in the chamber 1 is subjected to the one-stage sampling in the above-described embodiment, it is possible to utilize a two-stage sampling.

It should be noted that the chamber 1 includes a pressure fluctuation absorbing mechanism, not shown in figures, which is described later and absorbs the pressure fluctuation in the sealed space 1S caused by the sampling of the sampling unit 5. This pressure fluctuation absorbing mechanism might be configured to include, for example, an elastic body stretching in response to the pressure fluctuation in the sealed space 1S, or the like.

Although the brake of the four-wheeled vehicle is tested in the above-described embodiment, it is possible to test the brake of a two-wheeled vehicle. In addition, the test vehicle V might be not only an engine vehicle, but also a FCV (fuel cell vehicle), an EV (electric vehicle), a HV (hybrid vehicle), a motorcycle, or the like.

Although the vehicle V in the above-described embodiment is a completed vehicle, the present invention is not limited to this. It is possible to utilize a part of the completed vehicle.

Although the work load of the brake B in the above-described embodiment is calculated with the vehicle V driven on the chassis dynamometer 2, the present invention is not limited to this. It is possible to set the brake B on a brake dynamometer so as to calculate the work load of the brake B. In this case, the work load of the brake B could be calculated by a similar way to the above-described method, with the torque applied on the rotation axis of the flywheel included in the brake dynamo (corresponding to the "rotating body" of the present invention), the rotational speed of the rotation axis of the flywheel, and the time period during which the brake B is operated.

In addition, the arithmetic device 7 might utilize machine learning algorithm to calculate the brake dust amount. For example, the arithmetic device 7 includes a machine learning unit that performs machine learning with a learning data set consisted of data representing an elemental analysis result obtained by the elemental analysis unit 6 and data representing the brake dust amount, and utilizes a learning model generated by the machine learning unit so as to calculate the brake dust amount from the data representing the elemental analysis result obtained by the elemental analysis unit 6. It should be noted that the learning model might be generated by a machine learning device different from the arithmetic device 7.

In addition, the present invention is not limited to the above-described embodiment. It is needless to say that various modifications are possible without departing from the scope.

REFERENCE SIGNS LIST

100: Brake testing system
21: Chassis roller
22: Rotation control unit

3: Torque acquiring unit
71: Time period acquiring unit
72: Braking work load calculating unit

The invention claimed is:

1. A brake testing system of testing a brake of a vehicle driven on a bench having a rotating body, comprising:
   a rotation control unit that controls to make the rotating body rotate at a predetermined rotational speed;
   a torque acquiring unit that acquires a torque value generated on the rotating body by the brake of the vehicle being operated;
   a time period acquiring unit that acquires a time period during which the brake of the vehicle is operated;
   a braking work load calculating unit that calculates a work load of the brake based on the rotational speed of the rotating body controlled by the rotation control unit, the torque value acquired by the torque acquiring unit, and the time period acquired by the time period acquiring unit;
   a brake dust amount calculating unit that calculates a brake dust amount generated by the brake of the vehicle being operated; and
   a brake performance data generating unit that generates a set of brake performance data associating the brake dust amount calculated by the brake dust amount calculating unit and the work load of the brake calculated by the braking work load calculating unit.

2. The brake testing system according to claim 1, further comprising:
   a storing unit that associates and stores the brake dust amount calculated by the brake dust amount calculating unit and the work load of the brake calculated by the braking work load calculating unit.

3. The brake testing system according to claim 2, wherein the brake dust amount calculating unit acquires a weight value of a brake pad of the brake before an operation and a weight value of the brake pad of the brake after the operation, and calculates the brake dust amount based on these acquired weight values.

4. The brake testing system according to claim 2, further comprising:
   a sampling unit that performs sampling of air containing the brake dust generated by the brake being operated; and
   an elemental analysis unit that performs elemental analysis on the sampled air subjected to the sampling by the sampling unit,
   wherein the brake dust amount calculating unit calculates the brake dust amount contained in the sampled air based on an elemental analysis result of the elemental analysis unit.

5. The brake testing system according to claim 4, wherein the sampling unit performs the sampling of the air from in a vicinity of a wheel well unit of a wheel of the vehicle, in a vicinity of a brake caliper unit of the brake, or around the vehicle.

6. A brake testing method for testing a brake of a vehicle driven on a bench having a rotating body, comprising:
   a rotation control step for controlling to make the rotating body rotate at a predetermined rotational speed;
   a torque acquiring step for acquiring a torque value generated on the rotating body by the brake of the vehicle being operated;
   a time period acquiring step for acquiring a time period during which the brake of the vehicle is operated;
   a braking work load calculating step for calculating a work load of the brake based on the rotational speed of the rotating body controlled in the rotation control step, the torque value acquired in the torque acquiring step, and the time period acquired in the time period acquiring step;
   a brake dust amount calculating step for calculating a brake dust amount generated by the brake of the vehicle being operated; and
   a brake performance data generating step for generating a set of brake performance data associating the brake dust amount calculated in the brake dust amount calculating step and the work load of the brake calculated in the work load calculating step.

7. The brake testing method according to claim 6, further comprising:
   a storing step for associating and storing the brake dust amount calculated in the brake dust amount calculating step and the work load of the brake calculated in the work load calculating step.

8. The brake testing method according to claim 7, further comprising:
   a unit brake dust amount calculating step for calculating a unit brake dust amount which is a brake dust amount per unit work load of the brake.

9. A non-transitory program recording medium recorded with a program for a brake testing system to test a brake of a vehicle driven on a bench having a rotating body, the program making a computer implement:
   a function as a rotation control unit that controls to make the rotating body rotate at a predetermined rotational speed;
   a function as a torque acquiring unit that acquires a torque value generated on the rotating body by the brake of the vehicle being operated;
   a function as a time period acquiring unit that acquires a time period during which the brake of the vehicle is operated;
   a function as a braking work load calculating unit that calculates a work load of the brake based on the rotational speed of the rotating body controlled by the rotation control unit, the torque value acquired by the torque acquiring unit, and the time period acquired by the time period acquiring unit;
   a function as a brake dust amount calculating unit that calculates a brake dust amount generated by the brake of the vehicle being operated; and
   a function as a brake performance data generating unit that generates a set of brake performance data associating the brake dust amount and the work load of the brake.

* * * * *